(12) United States Patent
Isacsson et al.

(10) Patent No.: US 6,395,291 B1
(45) Date of Patent: May 28, 2002

(54) USE FOR PAIN MANAGEMENT

(75) Inventors: Göran Isacsson, Rönninge; Dag Selander, Göteborg, both of (SE)

(73) Assignee: Astra AB, Sodertalje (SE)

( * ) Notice: Subject to any disclaimer, the term of this patent is extended or adjusted under 35 U.S.C. 154(b) by 0 days.

(21) Appl. No.: 09/254,382

(22) PCT Filed: Jan. 11, 1999

(86) PCT No.: PCT/SE99/00012

§ 371 (c)(1),
(2), (4) Date: Mar. 2, 2000

(87) PCT Pub. No.: WO99/37301

PCT Pub. Date: Jul. 29, 1999

(30) Foreign Application Priority Data

Jan. 21, 1998 (SE) .............................. 9800139

(51) Int. Cl.⁷ ........................... A61F 13/00; A61K 9/00; A61K 6/00; A61K 9/14
(52) U.S. Cl. ..................... 424/422; 424/400; 424/401; 424/489
(58) Field of Search ............................... 424/400, 422, 424/401, 489

(56) References Cited

U.S. PATENT DOCUMENTS

| | | | |
|---|---|---|---|
| 5,856,342 A | 10/1999 | Eek ............................ | 514/330 |
| 5,962,532 A | 10/1999 | Campbell et al. ........... | 514/627 |

FOREIGN PATENT DOCUMENTS

| | | | |
|---|---|---|---|
| EP | 151 110 | 3/1989 | ......... C07D/211/60 |
| EP | 239 710 | 9/1990 | ......... C07D/211/60 |
| EP | 239710 B1 | 9/1990 | |
| WO | WO 85/00599 | 2/1985 | ......... C07D/211/60 |

OTHER PUBLICATIONS

Bendtsen, et al., "Qualitatively Altered Nociception in Chronic Myofascial Pain," *Pain* 65:259–264(1996).

Simons, et al., "Myofascial Origins of Low Back Pain, 1. Principles of Diagnosis and Treatment," *Postgraduate Medicine, Low Back Pain, Part 1* 73(2):66–73 (1983).

Tschopp, et al., "Local Injection Therapy in 107 Patients with Myofascial Pain Syndrome of the Head and Neck," *ORL* 58:306–310 (1996).

International Search Report for PCT/SE99/00012.

Simons et al., "Myofascial Origins of Low Back Pain; Principles of Diagnosis and a Treatment"; Postgraduate Medicine; p. 66–73, 1983.

Papa et al., "Anaesthetic Trigger Point Block: Ropivacaine vs. Bupivacaine," Abstract, Myopain 98, 4th World Congress on Myofascial Pain and Fibromyalgia, silva Marina, Italy, Aug. 24–27, 1998, p. 53.*

* cited by examiner

*Primary Examiner*—Thurman K. Page
*Assistant Examiner*—S. Tran
(74) *Attorney, Agent, or Firm*—Pillsbury Winthrop LLP

(57) ABSTRACT

The present invention is directed to the intramuscular use of ropivacaine for the manufacture of a medicament for use in the treatment of muskuloskeletal pain, in particular myofascial pain and tendinitis.

5 Claims, 1 Drawing Sheet

The individual baseline and follow-up patient data on pain VAS score at maximal mouth opening using a 100 mm graded VAS.

 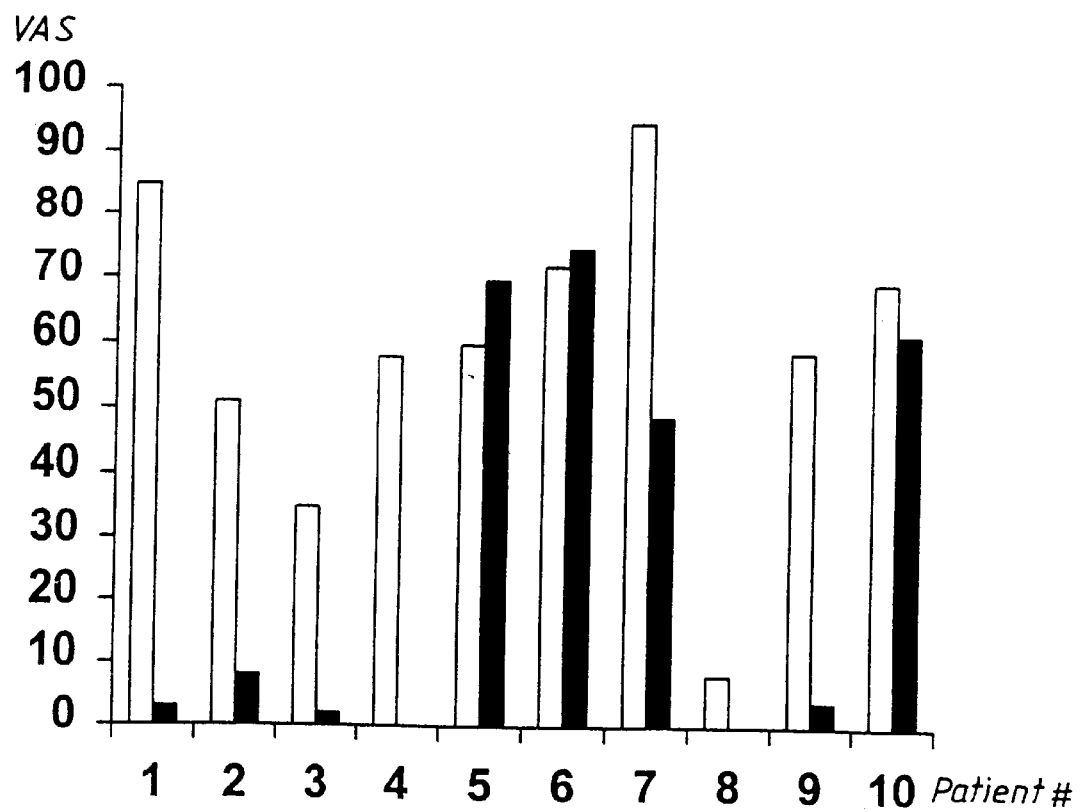
Fig. 1 The individual baseline and follow-up patient data on pain VAS score at maximal mouth opening using a 100 mm graded VAS.

USE FOR PAIN MANAGEMENT

CROSS REFERENCE TO RELATED APPLICATIONS

The present application represents U.S. national stage of international application PCT/SE99/00012 with an international filing date of Jan. 11, 1999. The international application claims priority to Swedish application 9800139-9, which was filed on Jan. 21, 1998.

FIELD OF THE INVENTION

The present invention is directed to the intramuscular use of ropivacaine for the manufacture of a medicament for use in the treatment of muskuloskeletal pain, in particular myofascial pain and tendinitis.

BACKGROUND AND PRIOR ART

The most common diagnosis in most pain clinics is a disorder of skeletal muscle and connective tissue origin, which may stem from previous trauma, muscle tension or postural abnormalities. The two dominating muscle pain disorders are the generalized condition fibromyalgia and the mainly localized myofascial pain. Myofascial pain conditions are characterized by discrete tender loci known as trigger points or tender points. These points are located by several methods including digital palpation or pressure pain threshold algometer testing and sometimes detection of skin loci with lowest electrical independence. The pathophysiology of human myofascial pain remains unknown. However, it has been suggested that myofascial tenderness may be the result of a lowered pressure pain threshold, a stronger response to presuures in the noxious range (Jensen K, *Quantification of tenderness by palpation and use of pressure algometers; In: friction Jr, Awad E., Advances in pain Research and Therapy*, Vol. 17, Raven press, New York, 199, 1990, pp. 165–181). The nociceptive processes are also qualitatively altered in patients with chronic myofascial pain indicating that myofascial pain may be mediated by low-threshold mechanosensitive afferents projecting to sensitized dorsal horn neurons (Bendsten L., Jensen R, Oleson J. *Qualitatively altered nociception in Chronic Myofascial pain, Pain* 1996; 65: pp. 259–264 ).

A wide range of therapeutic methods have been used over the years in order to cure long lasting myofascial pain. The mostly used methods have been massage, TENS, acupuncture, heat or cold packs, relaxation, unloading aching structures, traction and manipulation. Various analgesics, anti-inflammatory drugs and injected corticosteroids have also been used. The various treatments often give initial relief of pain but the pain often recurs thereby necessitating repeated treatments.

In a double-blind study of myofascial pain syndrome (MPS), the effect on pain has been compared between bupivacaine (0.25%), lignocaine (1%), and saline (Tschopp K P, Gysin C. *Local Injection therapy in* 107 *patients with myofascial pain syndrome of the head and neck;* J. Oto-Rhino-Laryng & Rel. Spec. 1996; 58: 306–310). No significant difference between these compounds has, however, been reported.

Outline of the Invention

The problem underlying the present invention was to find a new way of therapy for muskuloskeletal pain, in particular myofascial pain and tendinitis. The inventors of the present invention have found that the local anaesthetic ropivacaine is useful for the just mentioned therapy.

Ropivacaine refers to (S)-(−)-i-propyl-2',6'-pipecoloxylidide hydrochloride known to be useful for injection. It is described, including its long lasting local anesthetic effects, in EP 151 110 B1. In particular ropivacaine can be used in the form of its monohydrate in high enantiomeric purity, disclosed in EP 239 710 B1.

However, the routes of administration previously disclosed for ropivacaine, are epidural administration, nerve block and peripheral infiltration. Hitherto ropivacaine has not been disclosed for the therapeutic use in accordance with the present invention.

The present invention is thus directed to a new use of ropivacaine for the manufacture of a medicament for use in the treatment of muskuloskeletal pain, in particular myofascial pain.

The medical indication "muskuloskeletal pain" is a well established condition, and will be appreciated by a person skilled in the art.

The medical indication "myofascial pain" is defined as a regional pain complaint; pain complaint or alterred sensation in the expected distrubution of referred pain from a myofascial trigger point; taut band palpable in an accessible muscle; exquisite spot tenderness at one point along the length of the taut band; some degree of restricted range of motion, when measurable. A person skilled in the art will however appreciate the medical pain conditions belonging to this specific pain indication.

A further specific medical condition which is within the scope of the definition muskuloskeletal pain, is "tendinitis". A person skilled in the art will appreciate what patients belong to this group, but the following can however be mentioned as characterizing symptoms: regional pain complaint; localized tenderness; increased pain on movement; and limited range of motion.

"Trigger point" (TP) is a focus of hyperirritability in a muscle or its fascia that causes the patient pain. It causes referred pain and tenderness at rest, or with motion. The trigger point is always tender, and is located in a palpable band of muscle fibers. It prevents full lengthening of the muscle. It usually weakens the muscle, refers pain on direct compression, and mediates a local twitch response of the palpable band of muscle fibres when mechanically stimulated. Myofascial TPs can initiate referred autonomic phenomena, which generally appear in the pain reference zone.

A further aspect of the present invention is a method for the treatment of muskuloskeletal pain, in particular myofascial pain and tendinitis, whereby ropivacaine is administered intramuscularly to a patient suffering from said pain condition.

The active substance ropivacaine which is used in accordance with the present invention, is administered intramuscularly by injection in muscular "tender and/or trigger points". A "tender point" is defined as a point over a muscle/tendon which is tender and elicits palpabral reflex on digital palpation. Although the definition of tender points and trigger points differ slightly, the two words are used interchangeably.

Ropivacaine is administered as a formulation suitable for intramuscular administration and in an amount effective to ameliorate pain.

Accordingly, 0.1–10 ml ropivacaine is injected intramuscularly, preferably directly into each tender or trigger point. The concentration of ropivacaine for administration intramuscularly is preferably 1–20 mg/ml, more preferably 2–10 mg/ml. A concentration as low as 2–5 mg/ml may advantageously be used.

Biological Evaluation

Ropivacaine hydrochloride 7.5 mg/ml solution for injection was used (Naropin®, Astra AB, Sweden). Ropivacaine was administered as a single dose intramuscular tender point (TP) injection. Injection by means of one needle insertion per tender point was preceded by aspiration before infiltrating the study drug over the entire tender area. A standard disposable syringe with a 0.4 mm diameter needle was used. Injection rate was about 1 ml/30 sec. Injections were made at one occassion at a visit to the clinic. Follow-up data were obtained at a study end visit to the clinic 1 week after the injection.

(I) Patient Characteristics

Prior to the treatment the following information was recorded.

Demographic data: Date of birth, gender, race, body weight and height.

Past and current diagnoses: allergy and information related to significant past or present medical and surgical diagnoses excluding minor self-healing conditions with no obvious importance for the purpose of this study.

Current medication.

Active alcohol or drug abuse (yes/no).

A case history information including the duration of the present orofacial muscle pain was collected. A clinical examination of the orofacial region including digital palpation of the temporomandibular joints and masticatory muscles.

10 patients (5 men and 5 women) whose age varied from 19 years up to 69 years (mean 42.9 years of age) were included in this test. The duration of complaints ranged from 1 month and up to 10 years (mean 26.5 months).

All patients were subjected to unilateral injections of ropivacaine into tender points of the masseter muscle. Three patients received 1 ml, 5 patients received 2 ml, 1 patient received 3 ml and 1 patient received 4 ml of the study drug.

(II) Clinical Measurements (i) Pain on Maximal Mouth Opening

The patient rated their pain on a 100 mm visual analogue scale (VAS). On the VAS, 0 represents "no pain" and 100 represents "worst pain imaginable". The primary efficacy variable was VAS pain score at maximal mouth opening. The patient was asked to open the mouth as much as possible and then they rated the experienced pain.

(ii) Pain at Rest

The non-functional pain (aw at rest) was also assessed by the patient on the VAS scale. This parameter was rated before the rating of pain on maximal mouth opening.

(iii) Tender Muscular Points

A tender point was defined as point over a muscle/tendon which was tender and elicited a palpabral reflex on digital palpation. Bilateral digital palpation of the temporalis muscle, the masseter muscle, the lateral pterygoid muscle and the temporalis tendon was used for the registration of tender points. The number and site of injected tender points and the total amount of the study drug used were recorded. The assessment of tender muscle points was made prior to the assessment of range of movement.

(iv) Range of Movement

The distance between the edges of the right upper and the corresponding lower medial incisor was used for the measurements of maximum mouth opening. Both maximum opening with and without pain was registered.

Results

The primary efficacy parameter, VAS rated pain at maximal mouth opening, showed a dramatic reduction as a result of the treatment. The median VAS value at baseline was 59.5 mm compared to 6 mm at the follow-up. The data is shown in Table 1 below.

BRIEF DESCRIPTION OF THE DRAWING

FIG. 1 shows that 6 out of the 10 patients became free or almost free of their muscular pain. Also the pain at rest decreased significantly as the result of the treatment.

TABLE 1

Pain ratings using a 100 mm graded VAS at baseline and at follow-up.

|  | Pain at rest | | Pain at maximal jaw opening | |
| --- | --- | --- | --- | --- |
|  | Baseline | Follow-up | Baseline | Follow-up |
| Median | 19.5 | 3.5 | 59.5 | 6 |
| Mean | 33.3 | 3.7 | 59.3 | 27.3 |
| Min | 3 | 0 | 8 | 0 |
| Max | 89 | 16 | 95 | 75 |
| S.D. | 31.05 | 4.83 | 24.73 | 32.34 |

At baseline, 2 patients experienced pain every day and 8 patients pain several times per week. At the follow-up 6 patients had not a single episode with pain during the week prior to follow-up, 1 patient had pain at one occasion during the week and the remaining 3 patients had pain several times a week or every day.

What is claimed is:

1. A method for ameliorating myofascial pain in a patient, consisting of intramuscularly administering to said patient a composition consisting of ropivacaine as an active ingredient in an amount sufficient to ameliorate said pain and wherein said composition is administered at a trigger point.

2. The method of claim 1, wherein said ropivacaine is in its monohydrate form.

3. The method of either claim 1 or 2, wherein the concentration of administered ropivacaine is 1–20 mg/ml.

4. The method of claim 3, wherein the concentration of said ropivacaine is 1–10 mg/ml.

5. The method of claim 4, wherein the concentration of said ropivacaine is 2–5 mg/ml.

* * * * *